(12) United States Patent
Sakai et al.

(10) Patent No.: US 6,277,888 B1
(45) Date of Patent: Aug. 21, 2001

(54) DRUG COMPOSITION

(75) Inventors: Atsushi Sakai; Rumiko Masuda, both of Chikujo-gun (JP)

(73) Assignee: Welfide Corporation, Osaka (JP)

( * ) Notice: Subject to any disclaimer, the term of this patent is extended or adjusted under 35 U.S.C. 154(b) by 0 days.

(21) Appl. No.: 09/380,274

(22) PCT Filed: Feb. 25, 1998

(86) PCT No.: PCT/JP98/00755

§ 371 Date: Jan. 6, 2000

§ 102(e) Date: Jan. 6, 2000

(87) PCT Pub. No.: WO98/37875

PCT Pub. Date: Sep. 3, 1998

(30) Foreign Application Priority Data

Feb. 27, 1997 (JP) .................................................. 9-043668

(51) Int. Cl.[7] ..................... A61K 31/135; A61K 31/685; A61K 47/44
(52) U.S. Cl. ..................... 514/653; 514/78; 424/283.1
(58) Field of Search ................... 514/653, 78; 424/283.1

(56) References Cited

U.S. PATENT DOCUMENTS 4,323,563    4/1982    Takami et al. .

FOREIGN PATENT DOCUMENTS

| 0 426 029 | 5/1991 | (EP) . |
|---|---|---|
| 0 627 406 A1 | 12/1994 | (EP) . |
| 0 778 263 A1 | 6/1997 | (EP) . |
| 0 812 588 A1 | 12/1997 | (EP) . |
| 1172 814 | 8/1986 | (JP) . |
| 6 1172 814 | 8/1986 | (JP) . |
| 63-152327 | 6/1988 | (JP) . |
| 3-169807 | 5/1991 | (JP) . |
| 04173736 | 6/1992 | (JP) . |
| 06340525 | 12/1994 | (JP) . |

*Primary Examiner*—William R. A. Jarvis
*Assistant Examiner*—Vickie Kim
(74) *Attorney, Agent, or Firm*—Crowell & Moring, L.L.P.

(57) ABSTRACT

The present invention provides a pharmaceutical composition containing 2-amino-2-[2-(4-octylphenyl)ethyl]propane-1,3-diol or a pharmaceutically acceptable acid addition salt thereof and a lecithin, and containing a saccharide if desired, which can be formulated into a liquid preparation, and which is suitable for the suppression of rejection in organ or bone marrow transplantation, for an immunosuppressive sustention therapy or for the treatment of autoimmune diseases.

13 Claims, No Drawings

DRUG COMPOSITION

TECHNICAL FIELD

The present invention relates to a pharmaceutical composition and a composition for a kit, both containing 2-amino-2-[2-(4-octylphenyl)ethyl]propane-1,3-diol or a pharmaceutically acceptable acid addition salt thereof as an active ingredient. More particularly, the present invention relates to a pharmaceutical composition containing 2-amino-2-[2-(4-octylphenyl)ethyl]propane-1,3-diol or a pharmaceutically acceptable acid addition salt thereof and a lecithin, which is suitable for the suppression of rejection in organ (e.g., kidney, liver, heart, small intestine and the like) or bone marrow transplantation, for immunosuppressive sustention therapy or for the treatment of autoimmune diseases, and which can be formulated into a liquid preparation.

BACKGROUND ART

2-Amino-2-[2-(4-octylphenyl)ethyl]propane-1,3-diol and a pharmaceutically acceptable acid addition salt thereof are known to be useful as a suppressant of rejection in organ or bone marrow transplantation or as a therapeutic agent of various autoimmune diseases such as psoriasis, Behçet's disease and the like and rheumatic diseases, as described in, for example, WO94/08943.

The above-mentioned WO94/08943 discloses a preparation of said compound as an injection, and the solubilizers therefor disclosed are polyethylene glycol and ethanol. Nevertheless, polyethylene glycol shows undesirable effects such as local irritation and hemolysis, and the use thereof will be limited. In addition, ethanol is unapplicable to injections due to the local irritation it causes.

When the above-mentioned compound, particularly 2-amino-2-[2-(4-octylphenyl)ethyl]propane-1,3-diol hydrochloride (hereinafter sometimes referred to as the present compound throughout the specification) is dissolved in distilled water to make a liquid preparation, the liquid preparation obtained problematically causes hemolysis and local irritation. Even a liquid preparation containing the present compound and an isotonizing agent, such as sodium chloride, as an additive ordinarily employed for a liquid preparation, such as an injection or an eye drop, could not reduce hemolysis and local irritation, and the preparation was not satisfactory.

Japanese Patent Examined Publication No. 48485/1975 discloses that a lecithin, particularly egg yolk lecithin, does not show hemolysis. However, this publication does not teach that lecithin relieves hemolysis by the active ingredient compound. Further, Japanese Patent Unexamined Publication No. 340525/1994 discloses an eye drop characteristically containing vitamin A, hydrogenated lecithin and nonionic surfactant at a particular ratio in order to stabilize vitamin A and relieve irritation to the eye. This publication describes that, since a nonionic surfactant to be added to vitamin A, which is the active ingredient, causes irritation to the eye and, in order to relieve the irritation, hydrogenated lecithin is added at a ratio of 0.1 to 1 part per part of vitamin A, and 0.01 to 1 part per part of nonionic surfactant.

DISCLOSURE OF THE INVENTION

In view of the above situation, the present inventors have made intensive studies in an attempt to obtain a pharmaceutical composition containing 2-amino-2-[2-(4-octylphenyl)ethyl]propane-1,3-diol or a pharmaceutically acceptable acid addition salt thereof, which is associated with less side effects, such as hemolysis and local irritation, and which can be prepared into a liquid preparation such as an injection and an eye drop, and found that the addition of lecithin achieves the objects, which resulted in the completion of the present invention.

Accordingly, the present invention relates to a pharmaceutical composition containing 2-amino-2-[2-(4-octylphenyl)ethyl]propane-1,3-diol or a pharmaceutically acceptable acid addition salt thereof and lecithin, which can be easily prepared into a pharmaceutical preparation, which is associated with less side effects such as hemolysis, and which causes less local irritation, and therefore is suitable for a liquid preparation. The present invention has also noted that the addition of a saccharide selected from monosaccharides, disaccharides and sugar alcohols to said composition results in a liquid composition further improved in irritation. The pharmaceutical composition of the present invention, for example in the form of an injection, can remarkably relieve irritation to the skin, blood vessel and the like. The pharmaceutical composition of the present invention contains lecithin in a proportion of not less than 5 parts by weight, generally 5–300 parts by weight, per part by weight of the active ingredient compound. By adding lecithin in a proportion of particularly 5–100 parts by weight, preferably 5–50 parts by weight, more preferably 5–20 parts by weight, per part by weight of the active ingredient compound, hemolysis and local irritation caused by the active ingredient compound can be remarkably relieved.

The pharmaceutical composition of the present invention contains 2-amino-2-[2-(4-octylphenyl)ethyl]propane-1,3-diol or a pharmaceutically acceptable acid addition salt thereof as an active ingredient, lecithin and, if desired, a saccharide.

The active ingredient, 2-amino-2-[2-(4-octylphenyl)ethyl]propane-1,3-diol and a pharmaceutically acceptable acid addition salt thereof, of the pharmaceutical composition of the present invention can be produced by the method disclosed in WO94/08943. Preferred compound is 2-amino-2-[2-(4-octylphenyl)ethyl]propane-1,3-diol hydrochloride. Examples of other acid addition salt include hydrobromide, sulfate, acetate, fumarate, maleate, benzoate, citrate, malate, methanesulfonate and benzenesulfonate.

2-Amino-2-[2-(4-octylphenyl)ethyl]propane-1,3-diol or a pharmaceutically acceptable acid addition salt thereof is added in a proportion of 0.01–20% by weight, particularly 0.1–10% by weight, of the total weight of the composition.

The lecithin to be used in the present invention is, for example, egg yolk lecithin, soybean lecithin and the like, or hydrogenated lecithin. For greater amounts of the active ingredient compound to be dissolved and higher transparency of the obtained liquid to be achieved, preferred lecithin is that having a high phosphatidylcholine content and a high iodine value, in which lysophosphatidylcholine and phosphatidylethanolamine are detected in small amounts. For example, preferred egg yolk lecithin is one containing phosphatidylcholine in a proportion of 65–95% and having an iodine value of about 60–80, in which lysophosphatidylcholine and phosphatidylethanolamine are contained in small amounts. Of these, purified egg yolk lecithin recited in the Japanese Pharmaceutical Codex is most suitable. By hydrogenated lecithin is meant lecithin having higher resistance to oxidation, which is attributable to the addition of hydrogen. It is specifically exemplified by hydrogenated egg yolk lecithin and hydrogenated soybean lecithin. These hydrogenated lecithins preferably have an iodine value of not less than 6. These lecithins to be used in the present invention are added in an amount of not less than 5 parts by weight, ordinarily 5–300 parts by weight, particularly 5–100 parts by weight, preferably 5–50 parts by weight, more preferably 5–20 parts by weight, per part by weight of the above-mentioned active ingredient.

The saccharide to be used in the present invention is selected from monosaccharides, disaccharides and sugar alcohols, such as glucose, fructose, D-maltose, lactose, sucrose, D-mannitol, D-xylitol and D-sorbitol, which may be used alone or in combination. These saccharides are added in an amount of 1–100 parts by weight, particularly 5–80 parts by weight, per part by weight of 2-amino-2-[2-(4-octylphenyl)ethyl]propane-1,3-diol or a pharmaceutically acceptable acid addition salt thereof.

The preparation form of the pharmaceutical composition of the present invention is a liquid, which is specifically an injection, an eye drop, a nasal drop, an ear drop, a transfusion, an oral liquid, a liquid for inhalant, a liquid for lotion or the like, with preference given to an injection (e.g., intravenous, subcutaneous, intramuscular, etc.), an eye drop and a transfusion, with particular preference given to an injection (e.g., intravenous, subcutaneous, intramuscular, etc.) and a transfusion. These preparation forms are suitably selected according to the diseases to be treated, symptoms thereof, sex and age of the patient, application site and the like, and the preparation is formulated by a method known to those of ordinary skill in the art.

The pharmaceutical composition of the present invention can be placed in the market as a completed liquid preparation or a kit including a powder or a lyophilized product containing the active ingredient etc and a liquid for dissolution. For example, a solution obtained by dissolving the active ingredient, 2-amino-2-[2-(4-octylphenyl)ethyl]propane-1,3-diol or a pharmaceutically acceptable acid addition salt thereof (particularly hydrochloride), in purified water is sterilized by filtration and filled in vials, then lyophilized in vacuo to give lyophilized products. Separately, an aqueous solution, which is a liquid for dissolution, is obtained by dissolving the lecithin to be used in the present invention and a saccharide as necessary in distilled water. The above-mentioned lyophilized product can be dissolved in such liquid for dissolution when in use. The liquid for dissolution is used in a 5- to 2000-fold amount (part by weight) relative to 2-amino-2-[2-(4-octylphenyl)ethyl]propane-1,3-diol or a pharmaceutically acceptable acid addition salt thereof. By distilled water is meant here distilled water for injection when an injection is intended. The above-mentioned lyophilized product is generally filled in vials, and after displacement with nitrogen, sealed with a rubber seal and then with an aluminum seal, whereby a long term preservation at room temperature becomes possible. The lecithin and a saccharide to be added as necessary may be contained in a lyophilized product along with the active ingredient, 2-amino-2-[2-(4-octylphenyl)ethyl]propane-1,3-diol or a pharmaceutically acceptable acid addition salt thereof, instead of in a liquid for dissolution as mentioned above. The amount of lecithin is not less than 5 parts by weight, ordinarily 5–300 parts by weight, particularly 5–100 parts by weight, preferably 5–50 parts by weight, more preferably 5–20 parts by weight, per part by weight of the above-mentioned active ingredient. The amount of the saccharide to be added as necessary is 1–100 parts by weight, particularly 5–80 parts by weight, per part by weight of the above-mentioned active ingredient.

The pharmaceutical composition of the present invention may contain, in addition to the above-mentioned ingredients, for example, solvents, isotonizing agents, pH adjusting agents, buffering agents, antioxidants, thickeners, surfactants, preservatives, humectant, aromatics, coloring agents and the like as appropriate. These additives may be added when preparing the composition of the present invention into a pharmaceutical preparation or may be added to the liquid for dissolution contained in the above-mentioned kit preparation, which is used for dissolution when in use.

The pharmaceutical composition of the present invention can be used in the form of a liquid preparation for the suppression of rejection after organ or bone marrow transplantation, immunosuppressive sustention therapy, and treatment of eye diseases such as Behçet's disease and uveitis, and dermatitis inclusive of psoriasis, atopic dermatitis, contact dermatitis and allergic dermatitis. More specifically, the composition of the present invention can be used for the prophylaxis and treatment of various applicable diseases (e.g., immunosuppression for organ or bone marrow transplantation, various autoimmune diseases, various allergic diseases and the like) conventionally performed with oral preparations.

The composition of the present invention can be used, in the form of a liquid preparation, for the treatment or prophylaxis of resistance or rejection in organ or tissue transplantation (e.g., transplantation of the heart, kidney, liver, lung, bone marrow, cornea, pancreas, small intestine, limb, muscle, nervous, fatty marrow, duodenum, skin and pancreatic islet cell, and xeno-transplantation), graft-versus-host (GvH) diseases due to bone marrow transplantation, autoimmune diseases such as rheumatoid arthritis, systemic lupus erythematosus, nephrotic syndrome lupus, Hashimoto's thyroiditis, multiple sclerosis, myasthenia gravis, type I diabetes mellitus, type II adult onset diabetes mellitus, uveitis, nephrotic syndrome, steroid-dependent and steroid-resistant nephrosis, palmoplantar pustulosis, allergic encephalomyelitis, glomerulonephritis, etc., and infectious diseases caused by pathogenic microorganisms. The composition of the present invention is also useful for treating inflammatory, proliferative and hyperproliferative skin diseases, and cutaneous manifestations of immunologically-mediated illnesses such as psoriasis, psoriatic arthritis, atopic eczema (atopic dermatitis), contact dermatitis and further eczematous dermatitises, seborrheic dermatitis, lichen planus, pemphigus, bullous pemphigoid, epidermolysis bullosa, urticaria, angioedemas, vasculitides, erythema, cutaneous eosinophilias, acne, alopecia areata, eosinophilic fasciitis, and atherosclerosis. More particularly, the composition of the present invention is useful in hair revitalizing, such as in the treatment of female or male pattern alopecia, or senile alopecia, by providing epilation prevention, hair germination, and/or a promotion of hair generation and hair growth.

The composition of the present invention is further useful in the treatment of respiratory diseases, for example, sarcoidosis, fibroid lung, idiopathic interstitial pneumonia, and reversible obstructive airways disease, including conditions such as asthma, including bronchial asthma, infantile asthma, allergic asthma, intrinsic asthma, extrinsic asthma and dust asthma, particularly chronic or inveterate asthma (e.g., late asthma and airway hyperresponsiveness), bronchitis and the like. The composition of the present invention may be also useful for treating hepatic injury associated with ischemia. The composition of the present invention is also applied to certain eye diseases such as conjunctivitis, keratoconjunctivitis, keratitis, vernal conjunctivitis, uveitis associated with Behcet's disease, keratitis, herpetic keratitis, conical cornea, dystorphia epithelialis corneae, keratoleukoma, ocular pemphigus, Mooren's ulcer, scleritis, Graves' ophthalmopathy, severe intraocular inflammation and the like.

The composition of the present invention is also useful for preventing or treating inflammation of mucosa or blood vessels (e.g., leukotriene B4-mediated diseases, gastric ulcer, vascular damage caused by ischemic diseases and thrombosis, ischemic bowel disease, inflammatory bowel disease (e.g., Crohn's disease and ulcerative colitis), necrotizing enterocolitis), or intestinal lesions associated with thermal burns. The composition of the present invention is further useful for treating or preventing renal diseases including interstitial nephritis, Goodpasture's syndrome, hemolytic uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, vitiligo vulgaris, ichthyosis vulgaris, photoallergic sensitivity and cutaneous T cell lymphoma; circulatory diseases including arteriosclerosis, aortitis, polyarteritis nodosa and amyocardosis; collagen disease including scleroderma, Wegener's granulomatosis and Sjögren's syndrome; adiposis; eosinophilic fasciitis; periodontal disease; nephrotic syndrome; hemolytic uremic syndrome; and muscular dystrophy.

Further, the composition of the present invention is indicated in the prophylaxis or treatment of diseases including intestinal inflammations or allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example, migraine, rhinitis and eczema.

The active ingredient of the pharmaceutical composition of the present invention, 2-amino-2-[2-(4-octylphenyl)ethyl] propane-1,3-diol and a pharmaceutically acceptable acid addition salt thereof, also have liver regenerating activity and/or activity of promoting hypertrophy and hyperplasia of hepatocytes. Therefore, they are useful for the treatment or prevention of hepatic diseases such as immunogenic diseases (e.g., chronic autoimmune liver diseases including autoimmune hepatitis, primary biliary cirrhosis and sclerosing cholangitis), partial liver resection, acute liver necrosis (e.g., necrosis caused by toxins, viral hepatitis, shock or anoxia), B-virus hepatitis, non-A/non-B hepatitis and cirrhosis.

The composition of the present invention is also indicated for use as antimicrobial composition, and thus may be used in the treatment of diseases caused by pathogenic microorganisms and the like. Further, the composition of the present invention can be used for the prevention or treatment of malignant rheumatoid arthritis, amyloidosis, fulminant hepatitis, Shy-Drager syndrome, pustular psoriasis, Behçet's disease, systemic lupus erythematosus, endocrine ophthalmopathy, progressive systemic sclerosis, mixed connective tissue disease, aortitis syndrome, Wegener's granulomatosis, active chronic hepatitis, Evans syndrome, pollinosis, idiopathic hypoparathyroidism, Addison disease (autoimmune adrenalitis), autoimmune orchitis, autoimmune oophoritis, cold hemagglutinin disease, paroxysmal cold hemoglobinuria, pernicious anemia, adult T cell leukemia, autoimmune atrophic gastritis, lupoid hepatitis, tubulointerstitial nephritis, membranous nephritis, amyotrophic lateral sclerosis, rheumatic fever, postmyocardial infarction syndrome and sympathetic ophthalmitis.

Moreover, the composition of the present invention can be used in combination with other immunosuppressant(s), steroid(s) (e.g., prednisolone, methylprednisolone, dexamethasone, hydrocortisone and the like) or nonsteroidal antiinflammatory agent. As other immunosuppressant, preferred is one particularly selected from azathioprine, brequinar sodium, cyclosporin, deoxyspergualin, mizoribine, mycophenolate 2-morphorinoethyl, rapamycin, tacrolimus monohydrate, leflunomide and OKT-3.

While subject to variation depending on the diseases to be treated, symptoms thereof, sex and age of patients, application site and the like, the composition of the present invention can exhibit preferable clinical effects by administering or applying a product containing the present compound in a proportion of 0.00001–20% by weight, preferably 0.0001–10% by weight, once to several times (e.g., 2–5 times) a day.

BEST MODE FOR EMBODYING THE INVENTION

The present invention is described in more detail in the following by referring to Examples and Comparative examples.

In the following Examples and Comparative examples, the proportions are all based on the weight unless otherwise specified. In the Examples, the present compound means 2-amino-2-[2-(4-octylphenyl)ethyl]propane-1,3-diol hydrochloride as described above.

EXAMPLE 1

An injection containing the present compound and having the following formulation is produced.

| Present compound | 0.03% |
|---|---|
| purified egg yolk lecithin | 1.0% |
| D-mannitol | 5.0% |

The above-mentioned composition is dissolved in distilled water for injection to give an injection (total amount 10 ml). Conventional additives such as preservatives can be added as necessary.

EXAMPLE 2

An injection containing the present compound and having the following formulation is produced.

| Present compound | 0.1% |
|---|---|
| hydrogenated egg yolk lecithin | 1.0% |
| D-mannitol | 5.0% |

The above-mentioned composition is dissolved in distilled water for injection to give an injection (total amount 10 ml). Conventional additives such as preservatives can be added as necessary.

EXAMPLE 3

An injection containing the present compound and having the following formulation is produced.

| Present compound | 0.1% |
|---|---|
| purified egg yolk lecithin | 1.0% |

The above-mentioned composition is dissolved in distilled water for injection containing conventional additives such as preservatives as necessary. After sterilization by filtration, the total amount of 10 ml is charged in a vial and lyophilized by a conventional method to give an injection.

EXAMPLE 4

An injection containing the present compound and having the following formulation is produced.

| | |
|---|---|
| Present compound | 0.1% |
| hydrogenated soybean lecithin | 1.0% |

The above-mentioned composition is dissolved in distilled water for injection containing conventional additives such as preservatives as necessary. After sterilization by filtration, the total amount of 10 ml is charged in a vial and lyophilized by a conventional method to give an injection.

EXAMPLE 5

An injection containing the present compound and having the following formulation is produced.

| | |
|---|---|
| Present compound | 0.1% |
| purified egg yolk lecithin | 2.0% |
| sodium chloride | 0.9% |

The above-mentioned composition is dissolved in distilled water for injection to give an injection (total amount 10 ml). Conventional additives such as preservatives can be added as necessary.

EXAMPLE 6

An injection containing the present compound and having the following formulation is produced.

| | |
|---|---|
| Present compound | 0.01% |
| purified egg yolk lecithin | 0.05% |
| D-mannitol | 5.0% |

The above-mentioned composition is dissolved in distilled water for injection to give an injection (total amount 10 ml). Conventional additives such as preservatives can be added as necessary.

EXAMPLE 7

An injection containing the present compound and having the following formulation is produced.

| | |
|---|---|
| Present compound | 0.01% |
| purified egg yolk lecithin | 0.5% |
| D-mannitol | 5.0% |

The above-mentioned composition is dissolved in distilled water for injection to give an injection (total amount 10 ml). Conventional additives such as preservatives can be added as necessary.

EXAMPLE 8

An injection containing the present compound and having the following formulation is produced.

| | |
|---|---|
| Present invention | 0.1% |
| purified egg yolk lecithin | 0.6% |
| sucrose | 10.0% |

The above-mentioned composition is dissolved in distilled water for injection. After sterilization by filtration, the total amount of 2 ml is charged in a vial and lyophilized by a conventional method to give an injection. Conventional additives such as preservatives can be added as necessary.

EXAMPLE 9

An injection containing the present compound and having the following formulation is produced.

| | |
|---|---|
| Present Compound | 0.1% |
| purified egg yolk lecithin | 0.6% |
| D-maltose | 10.0% |

The above-mentioned composition is dissolved in distilled water for injection. After sterilization by filtration, the total amount of 10 ml is charged in a vial and lyophilized by a conventional method to give an injection. Conventional additives such as preservatives can be added as necessary.

EXAMPLE 10

An injection containing the present compound and having the following formulation is produced.

| | |
|---|---|
| Present compound | 0.01% |
| purified egg yolk lecithin | 1.0% |

The above-mentioned composition is dissolved in distilled water for injection to give an injection (total amount 10 ml). Conventional additives such as preservatives can be added as necessary.

EXAMPLE 11

An injection containing the present compound and having the following formulation is produced.

| | |
|---|---|
| Present compound | 0.1% |
| purified egg yolk lecithin | 1.0% |
| D-mannitol | 5.0% |

The above-mentioned composition is dissolved in distilled water for injection to give an injection (total amount 10 ml). Conventional additives such as preservatives can be added as necessary.

EXAMPLE 12

The compositions described in Example 1 to 11 are dissolved in sterile purified water (conventional additives such as preservatives can be added as necessary) to give eye drops (total amount of each 10 ml).

Comparative Example 1

Present Compound 0.1%

The present compound is dissolved in distilled water for injection to give an injection (total amount 10 ml).

Comparative Example 2

| | |
|---|---|
| Present compound | 0.1% |
| sodium chloride | 0.9% |

The above-mentioned composition is dissolved in distilled water for injection to give an injection (total amount 10 ml).

Comparative Example 3

| | |
|---|---|
| Present compound | 0.03% |
| mannitol | 5.0% |

The above-mentioned composition is dissolved in distilled water for injection to give an injection (total amount 10 ml).

Comparative Example 4

| | |
|---|---|
| Present compound | 0.01% |
| D-mannitol | 5.0% |

The above-mentioned composition is dissolved in distilled water for injection to give an injection (total amount 10 ml).

Comparative Example 5

| | |
|---|---|
| Present compound | 0.1% |
| mannitol | 5.0% |

The above-mentioned composition is dissolved in distilled water for injection to give an injection (total amount 10 ml).

Experimental Example 1

A test solution (1.0 ml) was stood at 37° C. for 2 minutes and admixed with human heparin (10 U/ml) added blood (0.1 ml). After incubation for 30 minutes, the admixture was cooled with water and centrifuged at 3,000 rpm for 5 minutes. The supernatant was diluted with physiological saline and absorbance at 540 nm was measured according to the method of Inglot et al. [*Biochem. Pharmacol.*, vol. 17, p. 269 (1968)], based on which hemolysis rate was calculated. As a control, distilled water for injection was used. From the calculation of the hemolysis rate, it was found that the preparations of Examples 1–10 showed significant decrease in hemolysis. In contrast, the preparations of Comparative examples 1–4 showed hemolysis.

Experimental Example 2

The preparations of Examples 1 and 11 and the preparations of Comparative examples 3 and 5 were intravenously administered repeatedly to 5-week-old LEW rats for 5 days, and the presence or otherwise of local irritation was examined based on the swelling percentage of the tail {(diameter of tail of the group administered with the drug−diameter of tail of control)÷diameter of tail of control×100} as the index. As a result, the preparations of Examples 1 and 11 showed the tail swelling percentage of 0.5% and 0.7%, respectively, demonstrating noticeable decrease of local irritation. In contrast, the preparations of Comparative examples 3 and 5 showed the swelling percentage of 15.6% and 20.5%, respectively, indicating the presence of local irritation.

Experimental Example 3

Irritation to the eye can be evaluated according to the Short Term Test Method for ocular mucous membrane irritation test of preservatives for eye drop, as described in Science Study Report of the Ministry of Health and Welfare (1970).

INDUSTRIAL APPLICABILITY

A pharmaceutical composition suitable for a liquid preparation with less local irritation, which contains 2-amino-2-[2-(4-octylphenyl)ethyl]propane-1,3-diol or a pharmaceutically acceptable acid addition salt thereof, which composition being associated with less side effects such as hemolysis and capable of being formulated into a pharmaceutical preparation with ease, can be provided by adding lecithin and, where necessary, a saccharide to 2-amino-2-[2-(4-octylphenyl)ethyl]propane-1,3-diol or a pharmaceutically acceptable acid addition salt thereof.

What is claimed is:

1. A pharmaceutical composition comprising 2-amino-2-[2-(4-octylphenyl)ethyl]propane-1,3-diol or a pharmaceutically acceptable acid addition salt thereof as an active ingredient, and a lecithin.

2. The pharmaceutical composition of claim 1, wherein the lecithin is a member selected from the group consisting of lecithins and hydrogenated lecithins.

3. The pharmaceutical composition of claim 1, wherein the lecithin is contained in a proportion of 5–300 parts by weight per part by weight of the active ingredient.

4. The pharmaceutical composition of claim 1, further comprising a saccharide.

5. The pharmaceutical composition of claim 4, wherein the saccharide is one or more members selected from the group consisting of monosaccharides, disaccharides and sugar alcohols.

6. The pharmaceutical composition of claim 4 or claim 5, wherein the saccharide is one or more members selected from the group consisting of D-mannitol, glucose, D-xylitol, D-maltose, D-sorbitol, lactose, fructose and sucrose.

7. The pharmaceutical composition of claim 1, wherein the active ingredient is 2-amino-2-[2-(4-octylphenyl)ethyl]propane- 1,3-diol hydrochloride.

8. A composition for kit comprising a lyophilized product of 2-amino-2-[2(4-octylphenyl)ethyl]propane-1,3-diol or a pharmaceutically acceptable add addition salt thereof, and a liquid for dissolution comprising an aqueous solution containing a lecithin.

9. A composition for kit comprising a lyophilized product containing 2-amino-2-[2-(4-octylphenyl)ethyl]propane-1,3-diol or a pharmaceutically acceptable acid addition salt thereof and a lecithin, and a liquid for dissolution containing distilled water.

10. The pharmaceutical composition of claim 8 or claim 9, wherein the lecithin is contained in a proportion of 5–300 parts by weight per part by weight of the active ingredient.

11. The composition of claim 8 or claim 9, wherein a saccharide is further added to the lyophilized product and/or the liquid for dissolution.

12. The composition for kit of claim 8 or claim 9, wherein the pharmaceutically acceptable add addition salt of 2-amino-2-[2-(4-octylphenyl)ethyl]propane- 1,3-diol is hydrochloride.

13. A pharmaceutical composition comprising 2-amino-2-[2-(4-octylphenyl)ethyl]propane- 1,3-diol or a pharmaceutically acceptable add addition salt thereof, and a lecithin, which shows reduced local irritation.

* * * * *